United States Patent [19]

Mirzaee et al.

[11] Patent Number: 5,957,903
[45] Date of Patent: *Sep. 28, 1999

[54] VARIABLE STIFFNESS GUIDEWIRE

[75] Inventors: Daryush Mirzaee, Santa Clara; William Stephen Tremulis, Redwood City, both of Calif.

[73] Assignee: Advanced Cardiovascular Systems, Inc., Santa Clara, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/976,444

[22] Filed: Nov. 25, 1997

Related U.S. Application Data

[63] Continuation of application No. 08/115,371, Sep. 1, 1993, abandoned, which is a continuation of application No. 07/776,622, Oct. 15, 1991, abandoned.

[51] Int. Cl.⁶ .................................................. A61M 25/00
[52] U.S. Cl. .......................... 604/282; 128/772; 604/280
[58] Field of Search .............................. 128/772; 604/95, 604/280, 282

[56] References Cited

U.S. PATENT DOCUMENTS

| | | |
|---|---|---|
| 3,528,406 | 9/1970 | Jeckel . |
| 3,547,103 | 12/1970 | Cook ........................................ 128/772 |
| 4,020,829 | 5/1977 | Willson et al. ...................... 128/772 X |
| 4,215,703 | 8/1980 | Willson ................................... 128/772 |
| 4,456,017 | 6/1984 | Miles . |
| 4,676,249 | 6/1987 | Arenas et al. ....................... 128/772 X |
| 4,721,117 | 1/1988 | Mar et al. ................................ 128/772 |
| 4,724,846 | 2/1988 | Evans, III ............................... 128/772 |
| 4,757,827 | 7/1988 | Buchbinder et al. ................... 128/772 |
| 4,777,951 | 10/1988 | Cribier et al. ........................... 606/194 |
| 4,779,628 | 10/1988 | Machek .................................... 128/772 |
| 4,846,186 | 7/1989 | Box et al. ............................ 128/772 X |
| 4,873,983 | 10/1989 | Winters ................................ 128/772 X |
| 4,930,521 | 6/1990 | Metzger et al. ..................... 128/772 X |
| 4,932,419 | 6/1990 | de Toledo ................................ 128/772 |
| 4,940,062 | 7/1990 | Hampton et al. ....................... 128/772 |
| 4,944,727 | 7/1990 | McCoy ................................. 128/657 X |
| 4,951,677 | 8/1990 | Crowley et al. .................... 128/662.06 |
| 4,955,384 | 9/1990 | Taylor et al. ........................ 128/772 X |
| 4,964,409 | 10/1990 | Tremulis .................................. 128/657 |
| 4,981,478 | 1/1991 | Evard et al. ......................... 128/772 X |
| 5,007,434 | 4/1991 | Doyle et al. ......................... 128/657 X |
| 5,040,543 | 8/1991 | Badera et al. ....................... 128/657 X |
| 5,050,606 | 9/1991 | Tremulis .................................. 128/657 |
| 5,052,404 | 10/1991 | Hodgson ................................ 128/772 |
| 5,059,176 | 10/1991 | Winters ............................... 606/194 X |
| 5,060,660 | 10/1991 | Gambale et al. ....................... 128/772 |
| 5,063,935 | 11/1991 | Gambale ............................. 128/772 X |
| 5,065,769 | 11/1991 | de Toledo .............................. 128/772 |
| 5,069,217 | 12/1991 | Fleischhacker, jr. .................... 128/657 |
| 5,095,911 | 3/1992 | Pomeranz ........................... 128/772 X |
| 5,143,085 | 9/1992 | Wilson ................................ 128/657 X |
| 5,159,937 | 11/1992 | Tremulis ............................. 128/657 X |
| 5,165,421 | 11/1992 | Fleishhacker et al. ................. 128/772 |
| 5,184,627 | 2/1993 | de Toledo ........................... 604/282 X |

FOREIGN PATENT DOCUMENTS

| | | | |
|---|---|---|---|
| 4130042 | 10/1991 | Germany ................................. 128/772 |
| 57-54410 | 9/1980 | Japan . | |
| 9114394 | 10/1991 | WIPO .................................... 128/772 |

*Primary Examiner*—John G. Weiss
*Assistant Examiner*—Dennis Ruhl
*Attorney, Agent, or Firm*—Heller, Ehrman, White & McAuliffe

[57] ABSTRACT

Using a variable stiffness guidewire to cross a stenosed region of a patient's vasculature by advancing the distal end of the guidewire to the stenosed region, reducing the flexibility of the distal end of the guidewire, and further advancing the distal end through and past the stenosed region of the lumen. The variable stiffness guidewire has a longitudinally movable core member with a proximal end and a shapable distal end, a compressible body is slidably mounted on the core member, with one end of the compressible body secured to the end of the core member, and a tubular support member is disposed about the core member with a distal end that abuts the proximal end of the compressible body. The guidewire further comprises a tensioning means at the proximal end to move the core member longitudinally with respect to the tubular support member so as to compress and reduce the flexibility of the compressible body.

10 Claims, 2 Drawing Sheets

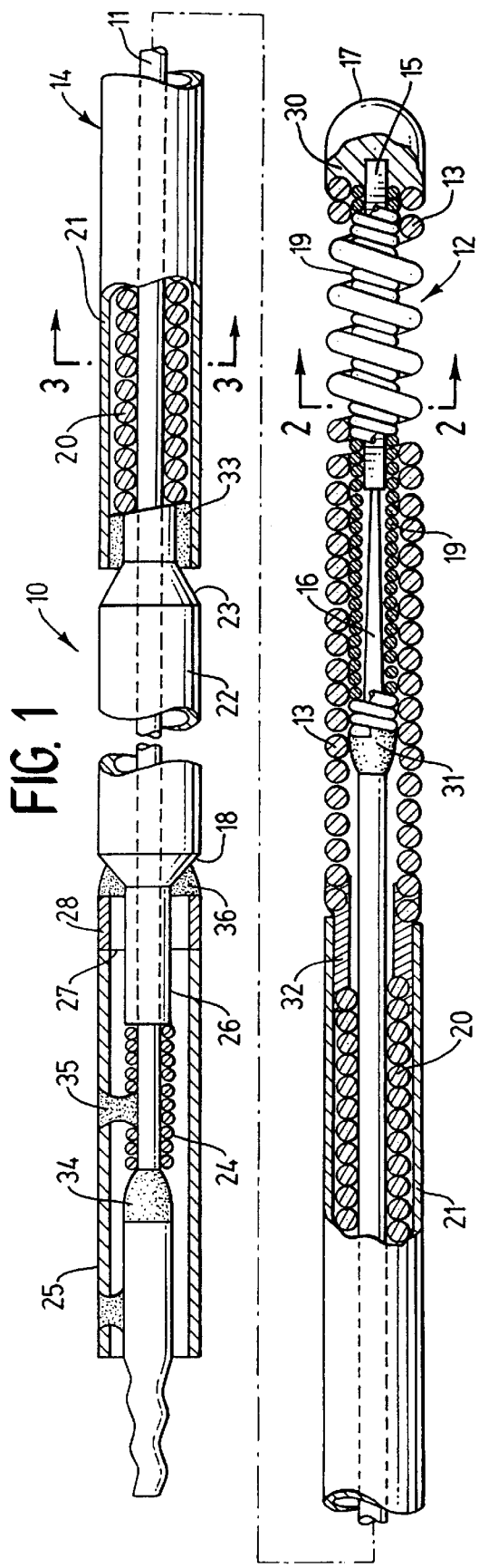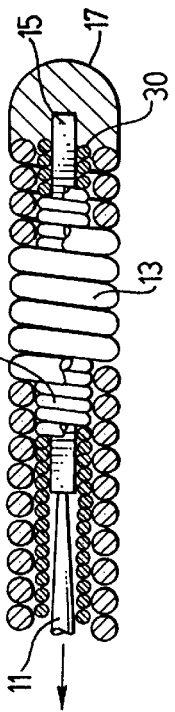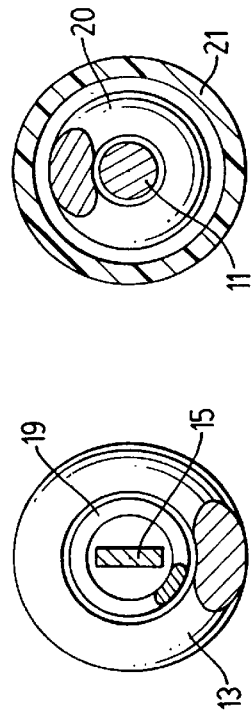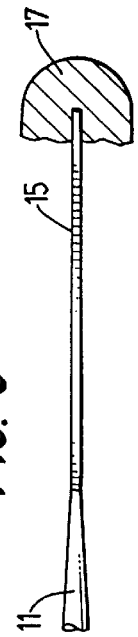

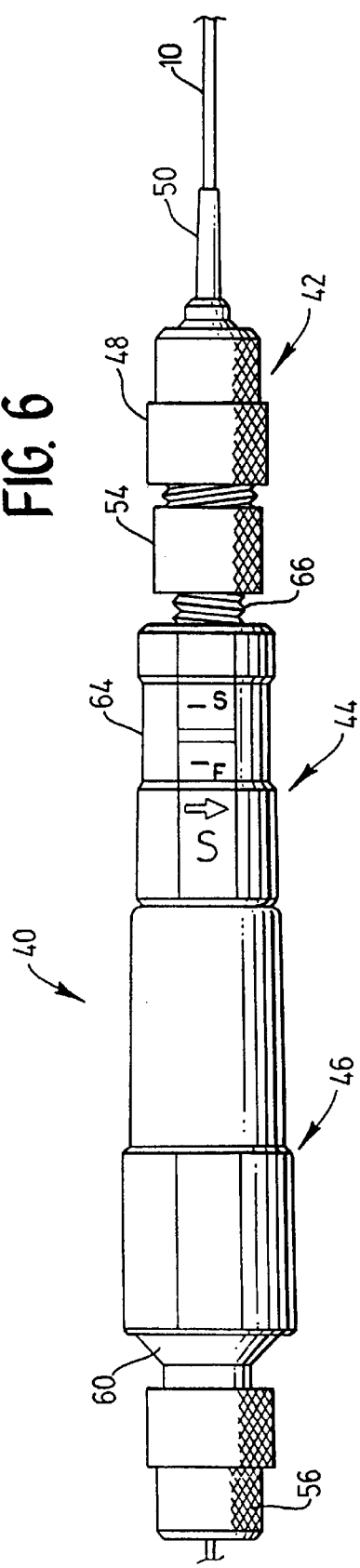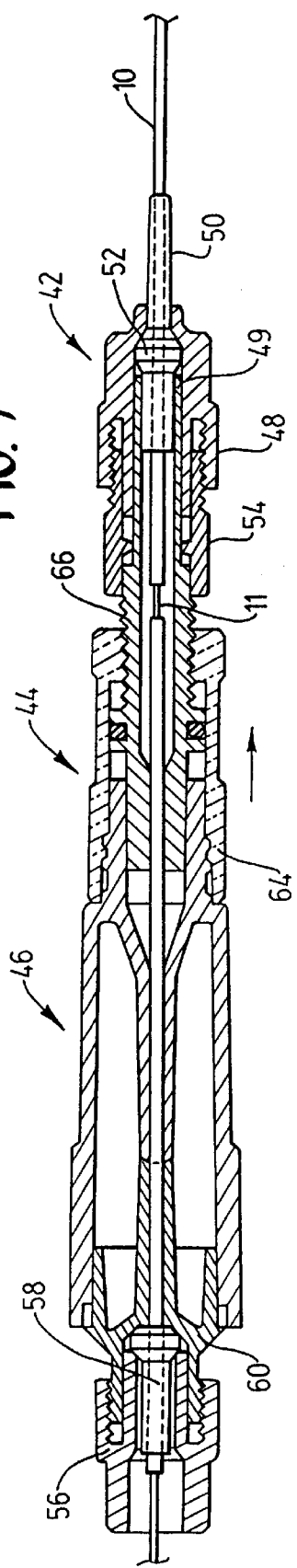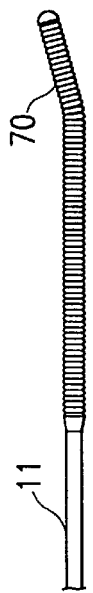

VARIABLE STIFFNESS GUIDEWIRE

This is a continuation of application Ser. No. 08/115,371, which was filed on Sep. 1, 1993 now abandoned, which is a continuation of Ser. No. 07/776,622, which was filed on Oct. 15, 1991 now abandoned.

BACKGROUND OF THE INVENTION

This invention relates to guiding means used to guide intraluminal devices through body lumens and particularly to guidewires used to advance catheters within body lumens in procedures such as percutaneous transluminal coronary angioplasty (PTCA).

In typical PTCA procedures a guiding catheter having a preformed distal tip is first percutaneously introduced into the vascular system of a patient using a Seldinger technique. The guiding catheter is then advanced through the peripheral vasculature until the distal end thereof reaches the ostium of the coronary artery most accessible to the artery to be dilated. The guiding catheter may then be torqued at the proximal end in order to seat the distal end of the guiding catheter in the ostium of the artery.

A balloon catheter assembly is formed by loading a guidewire through the inner lumen of a balloon dilatation catheter such that the distal tip of the guidewire extends out of the distal tip of the balloon catheter. The balloon catheter assembly is connected to an adapter at its proximal end; thereafter its distal end is inserted into the proximal opening of the guiding catheter and advanced therethrough until the distal tip of the balloon catheter assembly reaches the distal end of the seated guiding catheter. The guidewire is then advanced out of the distal end of the balloon catheter and through the coronary artery until the distal tip of the guidewire extends distally several centimeters of the lesion to be dilated, thus providing support to the dilatation catheter during the angioplasty procedure. Thereafter, the balloon catheter is advanced out of the distal end of the guiding catheter over the guidewire until it reaches a desired location within the artery to be dilated, e.g., when the balloon portion of the catheter traverses the stenotic lesion to be dilated.

Under model conditions, once the balloon catheter and guidewire have been properly positioned across a lesion, the balloon is inflated to compress the atherosclerotic plaque against the inside of the artery wall and to otherwise expand the inner lumen of the artery. The balloon is then deflated so that blood flow is resumed through the now dilated artery and the dilatation catheter assembly and guiding catheter are removed.

Conventional guidewires for angioplasty and other intravascular procedures are typically comprised of an elongated core member, with one or more tapered sections near the distal end; a helical coil which is disposed about the distal portion of the core member; and a shapable ribbon which extends within the flexible body and which is secured to the distal end of the helical coil by suitable means such as welding to form a rounded plug. A knob or handle may be provided on the proximal end of the core member to rotate and thereby steer the guidewire which is being advanced through a patient's vasculature. The shapable ribbon may either be formed by flattening the distal extremity of the core member or by attaching a separate ribbon which is secured to the distal extremity of the core member.

Further details of dilatation catheters, guidewires, and devices associated therewith for angioplasty procedures may be found in U.S. Pat. No. 4,323,071 (Simpson-Robert), U.S. Pat. No. 4,439,185 (Lundquist), U.S. Pat. No. 4,516,972 (Samson), U.S. Pat. No. 4,538,622 (Samson et al.), U.S. Pat. No. 4,554,929 (Samson et al.), U.S. Pat. No. 4,582,181 (now Re 33,166) (Samson), U.S. Pat. No. 4,616,652 (Simpson), U.S. Pat. No. 4,638,805 (Powell) and U.S. Pat. No. 4,748,982 (Horzewski et al.) which are hereby incorporated herein in their entirety by reference thereto.

It is not uncommon during an angioplasty procedure for the physician to be unable to cross a stenosis with the guidewire that was advanced through the patient's vasculature. In that event, the guidewire is usually removed and another guidewire with a stiffer distal tip is advanced through the patient's vasculature so that it can be pushed across the lesion. Frequently, however, the guidewire with the stiffer distal tip cannot be advanced through the patient's tortuous vasculature to the desired location without causing trauma to the vasculature.

Heretofore, physicians have been forced to select guidewires which either have increased pushability and decreased flexibility or guidewires with increased flexibility and decreased pushability. As a result of these selection constraints, physicians will typically attempt to anticipate the stiffness which will be needed to cross the stenosis to be dilated while avoiding a guidewire which may unduly increase the risk of vascular trauma to the patient. The difficulty with this trial and error method of selecting guidewires is that if the physician selects a guidewire with inappropriate characteristics, additional time must be spent removing the guidewire and inserting another more appropriate guidewire.

What has been needed and heretofore unavailable is a guidewire which has the flexible and steerable characteristics which enable the guidewire to traverse the patient's peripheral and coronary vasculature with little or no trauma, but which has means to increase the stiffness of the distal tip in order to facilitate crossing an occlusion.

SUMMARY OF THE INVENTION

The present invention is directed to an improved guidewire wherein the distal portion of the guidewire can be variably adjusted by the operator from a relatively flexible configuration to a stiffer configuration during an angioplasty procedure depending upon the particular requirements of the procedure.

The guidewire of the present invention has an elongated longitudinally movable core member with a flexible body, having a longitudinally compressible section, disposed about and secured to the distal end of the core member and an elongated tubular support member disposed about the remaining portion of the core member, proximal to the flexible body. The distal end of the core member is shapable or has a shapable member secured thereto. Means are provided at the proximal end for applying torque to the distal end of the core member in order to steer the shapable distal end of the guidewire through the patient's vasculature. Tensioning means are also provided for effecting longitudinal movement of the core member within the flexible body and tubular support member which increases tension on the core member. The increase in tension results in the compression of the compressible section of the flexible body which thereby increases the stiffness of the distal tip of the guidewire. Conversely, reducing the tension on the core member expands the compressed section and returns the distal tip to a more flexible condition. In a presently preferred embodiment, the flexible body is a helical coil with a section thereof expanded to provide compressibility.

A torquing means including a tensioning means is removably attached to the proximal end of the guidewire. The torquing means includes a distal clamping member and a proximal clamping member which secures the torquing means to the distal hypotube and proximal hypotube, respectively. A rotatable member connects the distal and proximal clamping members such that when the tensioning means is turned, the core wire 11 moves longitudinally in the proximal or distal direction relative to the outer member. Longitudinal movement of the core wire relative to the outer member changes the amount of stacking of the proximal coils which results in the distal tip becoming stiff or flexible.

In a typical application of the present invention, the physician loads the guidewire through the inner lumen of the balloon catheter until only the shaped distal tip of the guidewire extends out of the distal end of the balloon catheter. The balloon catheter and guidewire assembly are then advanced through the guiding catheter, the distal end thereof which has previously been seated in the ostium of the desired coronary artery, until the distal end of the balloon catheter and guidewire assembly reaches the distal end of the guiding catheter. The shaped distal end of the guidewire is then advanced out the distal end of the balloon catheter and through the patient's coronary arterial system until it crosses the stenosis to be dilated. The guidewire is then steered into the desired sidebranch of the artery by torquing the guidewire from its proximal end. If the physician is unable to push across the stenosis, the tensioning means provided on the proximal end of the guidewire may be employed to apply tension to the core member to stack the longitudinally compressible section, thus straightening and increasing the stiffness of the distal tip of the guidewire. The guidewire with the now stiffer distal tip can then more easily be pushed across the occlusion. Once the distal end of the guidewire has passed the occluded area, the tension on the core wire can be released to return the tip of the guidewire to a more flexible condition.

After the guidewire has crossed the occlusion, the balloon catheter is advanced out of the guiding catheter over the guidewire and into the target coronary artery, so that the balloon portion of the balloon catheter crosses the lesion to be dilated.

The invention provides for a guidewire which features a variably stiff, shapable distal tip which is capable, when in a relatively flexible condition, of being steered through the patient's vasculature without causing trauma thereto and, when in a relatively stiff condition, can be pushed through an occluded area.

BRIEF DESCRIPTION OF THE DRAWINGS

FIG. 1 is a centerline longitudinal view taken along the longitudinal axis of a guidewire which embodies the features of the present invention.

FIG. 2 is a cross-sectional view taken along the lines 2—2 in FIG. 1 of the guidewire assembly.

FIG. 3 is a cross-sectional view taken along the lines 3—3 in FIG. 1 of the guidewire assembly.

FIG. 4 is a cross-sectional view taken along the longitudinal axis of the distal tip section of the guidewire which embodies features of the present invention.

FIG. 5 is a cross-sectional view taken along the longitudinal axis of the distal tip section of the guidewire showing only the core wire, shaping section and tip. The cross-sectional view shown in FIG. 5 is taken 90 degrees from the view shown in FIG. 4.

FIG. 6 is a longitudinal view of the torquing and tensioney means of the present invention.

FIG. 7 is a centerline longitudinal view taken along the longitudinal axis of the torquing and tensioney means of the present invention.

FIG. 8 illustrates the shaped distal extremity of the guidewire.

DETAILED DESCRIPTION OF THE INVENTION

FIG. 1 illustrates a guidewire assembly 10 embodying features of the invention which generally includes an elongated longitudinally movable core member or wire 11 having a shapable distal section 12 and a tubular support member 14 disposed about the portion of the core member proximal to the helical coil 13.

The elongated longitudinally movable core wire 11 is typically 185 cm in length and is manufactured from stainless steel (304) that is about 0.0070 inches (0.01778 cm) in diameter. A coating is applied to the core wire 11 to reduce friction, e.g., polytetrafluoroethylene which is commercially sold under the trademark Teflon® by E. I. dupont, deNemours & Co., Wilmington, Del. The maximum outer diameter of the core wire 11, including the coating is approximately 0.0075 inch (0.01905 cm).

The distal most portion of the core wire 11 is flattened to form a shaping section 15 as illustrated in FIGS. 1, 4 and 5. From the point where the core wire has been flattened to form a shaping section 15, the shaping section has a rectangular cross-section as shown in FIG. 2 over a length of from about 0.8 to 1.6 (1.4) cm. The tapered section 16 of the core wire 11, which precedes the shaping section 15, has a first transverse cross-sectional diameter of from about 0.004 to 0.007 (0.0055) inch [0.0101 to 0.0178 (0.014) cm] over a length of 4.7 to 5.7 cm, and a second transverse cross-sectional diameter of from about 0.001 to 0.004 (0.0025) inch [0.0025 to 0.0102 (0.0064) cm] over a length of from 1.4 to 2.0 (1.7) cm.

The shapable distal end 12 is composed of the helical coil 13 and a tip or plug 17 which attaches to the distal end of the helical coil 13. The helical coil is generally fabricated from a radiopaque material, such as a platinum-nickel alloy, in order to enable the physicians to detect the location of the distal end of the guidewire assembly during the angioplasty procedure. During manufacture, the distal most 1 to 2 cm of the helical coil are stretched in order to allow the guidewire to assume a relatively flexible configuration at its guiding end during the angioplasty procedure. The wire which forms the helical coil 13 is fabricated from 0.0025 inch (0.00635 cm) in diameter wire, using a winding mandrel with an outer diameter of from about 0.0075 to 0.0085 (0.0080) inch [0.0190 to 0.0213 (0.0203) cm]. The resulting outer diameter of the helical coil 13 ranges from about 0.012 to 0.015 (0.0135) inch [0.031 to 0.038 (0.0345) cm]. The length of the entire shapable distal end 12, which includes the longitudinally helical coil 13 and tip 17, ranges from about 2.6 to 3.4 (3.0) cm.

The distal end of the core wire 11 is surrounded by a center coil 19 which is located along the inside length of the helical coil 13 and is characterized by smaller diameter wire with looser windings than the helical coil. The center coil controls the centering of the core wire 11 during the compacting of the helical coil 13. For example, if the core wire is attached eccentrically to the tip 17, increasing the tension on the core wire 11 will increase the stiffness of the shapable distal end 12 of the guidewire but the individual turns of the helical coil 13 will become offset giving the shapable distal end 12 a wavy appearance. The center coil 19 also helps to improve the strength of the shapable distal end 12 during transition from the relatively flexible to the relatively stiff conditions (shown in FIGS. 1 and 4). The center coil 19 is manufactured from 0.001 inch (0.00254 cm) diameter stainless steel wire using a winding mandrel of from about 0.0045 to 0.0055 (0.0050) inch [0.0114 to 0.0140 (0.0127) cm]. The resulting center coil has an outer diameter of 0.005 to 0.008 (0.0073) inch [0.0127 to 0.0203 (0.0185) cm] and is 40 to 60% stretched to provide a finished length of about 1.9 cm.

Typically, the helical coil 13, center coil 19 and core wire 11 are connected together by a suitable means such as a solder joint 30 at the distal end of the guidewire which is from 1.0 to 1.5 mm in length. The proximal end of the center coil is connected to the core wire by a solder joint 31 of from 0.5 to 1.0 mm in length. The helical coil 13 is connected to the intermediate coil 20 by a suitable means 32 such as a gold solder joint which is from 0.5 to 1.5 mm in length.

The tubular support member 14, having a proximal end and a distal end, may generally include one or more coiled sections. Preferably a plurality of coiled sections with distinctive coil windings may be connected in-line to form the tubular support member which has a range of flexibility characteristics along its length.

The distal end of the tubular support member 14 includes an intermediate coil 20 which has a length of from about 40.0 to about 44.0 (42.0) cm and is fabricated from 0.0020 inch in diameter stainless steel (304) wire using a winding mandrel with an outer diameter of from about 0.0070 to about 0.0090 (0.0080) inch [0.0178 to 0.0229 (0.0203) cm]. The resulting outer diameter of the intermediate coil 20 ranges from about 0.0116 to about 0.0132 (0.0124) inch [0.0295 to 0.0335 (0.0315) cm] with an inner diameter of at least 0.0085 inch (0.0216 cm) to accommodate the core wire 11. The the distal most coils, e.g. 3–8 coils, of the intermediate coil have a stretch of up to 125% in order to facilitate joining to another section. The intermediate coil 20 may be encased in an outer sleeve 21 which may be made from polysiloxane (e.g., Microglide®) coated polyimide and which has an outer diameter of from about 0.0140 to about 0.0150 (0.0145) inch [0.0356 to 0.0381 (0.0368) cm] and an inner diameter of from about 0.0130 to about 0.0140 (0.0135) inch [0.033 to 0.036 (0.034) cm] and is secured to the intermediate coil 20 at their distal ends by a suitable means such as a coil joint at the distal 32 and proximal 33 ends which may consist of an adhesive compound over 1.0 to 2.0 mm with a solder joint overlap of 1.5 to 2.0 cm.

A distal hypotube 22 is formed of stainless steel hypotubing with an outer diameter of from about 0.0130 to 0.0140 inch (0.033 to 0.36 cm) and an inner diameter from about 0.0076 to 0.0088 inch (0.019 to 0.022 cm) and a total length of about 120 to 140 cm. The hypotube may also be coated with a friction reducing coating, such as Teflon ®, with a maximum outer diameter of 0.0145 inch (0.0368 cm). The distal end 23 of the hypotube is tapered to an outer diameter of from about 0.0118 to 0.0126 (0.0122 ) inch [0.030 to 0.032 (0.031) cm] over a length of 2.0 to 3.0 cm at the distal end 23, and the proximal end 18 tapers over a length of 1.0 to 2.0 cm to form a hypotube overlap 26 with an outer diameter of 0.010 to 0.011 inch and a length of about 1.2 cm. The hypotube tapering at its proximal and distal ends 18,23, allow the ends to line-up against a proximal coil 24 and the intermediate coil 20, respectively, with the joined sections presenting a smooth outer surface.

The intermediate coil 20 and outer sleeve 21 are connected to the distal hypotube 22 at their proximal end by a joint 33 which may consist of a suitable adhesive such as Loctite™ 405 over a suitable length, e.g. 1.0 to 1.5 cm with an overlap of 1.5 to 2.0 cm.

The proximal most section of the tubular support member consists of a proximal hypotube which is typically manufactured from the same material as the distal hypotube, but which has an outer diameter of from 0.0135 to 0.0155 inch (0.034 to 0.039 cm) and an inner diameter of from 0.011 to 0.012 inch (0.02 to 0.03 cm) over a length of from 3.7 to 4.3 cm. The proximal hypotube has a seam 27 which separates the hypotube into a proximal section 25 and a hypotube stopper 28. The proximal hypotube section 25 abuts the hypotube stopper 28 to prevent the proximal hypotube 25 from being pushed further distally when the longitudinal tension on the core wire 11 is adjusted using the torquing means described below thus preventing an overstretch of the tip coil 12.

The proximal coil 24 which is proximal to the distal hypotube 22 has a length of from about 1.0 to 1.5 cm and is typically fabricated from stainless steel which is about 0.001 inch (0.00254 cm) in diameter and which has an outer diameter of about 0.009 to 0.011 inch (0.023 to 0.028 cm) and an inner diameter of 0.007 to 0.008 inch (0.018 to 0.020 cm) to accommodate the core wire 11.

The proximal coil 24 may be connected to the core wire 11 via a solder joint 34 which has a length of 1.5 to 2.0 mm and covers 4 to 8 coils which have been 30–40% stretched. The proximal coil 24, core wire 11 and proximal hypotube 25 are connected at a location proximal to the junction 27 by a suitable means such as a laser weld 35.

The hypotube stopper 28 which is distal to junction 27 is connected to the distal hypotube 22 by a joint 36 formed of a suitable adhesive such as Loctite™ 405, which typically has a length of 0.4 to 0.8 cm with an overlap of 0.3 to 0.8 cm.

When the guidewire is disposed within tortuous anatomy, manual movement of the core wire 11 can become difficult. To that end the torquing means 40 may be attached to the proximal end of the guidewire.

A torquing means 40, shown in FIGS. 6 and 7, fits over the proximal end of the guidewire 10 to allow torque and tension to be applied during an intravascular procedure. The torquing means 40 features a distal portion 42 which clamps onto the distal hypotube 22; a longitudinally movable tension effecting section 44; and a proximal portion 46 which clamps onto the proximal hypotube 25.

The distal portion 42 of the torquing means 40 has a threaded female distal cap 48 which fits over strain relief member 50 and a hollow distal collet 52. The hollow distal collet 52 secures the distal portion 42 of the torquing means 40 onto the distal hypotube 22. When the male portion 54 is screwed into the threaded female cap 48 they push the wedges 49 of the collet together and secure it onto the guidewire 10.

The longitudinally movable tension effecting section 44 has a rotating knob 64 and a threaded plunger 66. The tension effecting section 44 is connected to the proximal portion 46 of the torquing means and abuts against the distal portion 42 of the torquing means.

The proximal portion 46 of the torquing means 40 has a threaded proximal cap 56 which screws onto a cap body 60, and a hollow proximal collet 58 which secures the proximal portion 46 of the torquing means 40 onto the proximal hypotube 25 at a location proximal to the junction 27.

Increasing the tension on the core wire 11 causes the stretched coils of the shapable distal end 12 to become stacked (as illustrated in FIG. 4) so that the shapable distal end 12 of the guidewire 10 becomes stiffer as the tension is increased and the shaped distal extremity 70 (illustrated in FIG. 8) of the guidewire 10 is straightened to a coaxial orientation with the core. Tension may be adjusted by turning the rotating knob 64. Once the shapable distal end 12 of the guidewire has been stiffened and pushed through the lesion to be dilated, the physician can then release the tension on the core wire 11, thus allowing the helical coil 13 of the shapable distal end 12 to be returned to their stretched condition (illustrated in FIG. 1), resulting in the shapable distal end 12 of the guidewire 10 returning to its initial, relatively flexible configuration. Thus, the invention gives the physician the ability to control the tension at the proximal end during the procedure and to variably increase the amount of stacking of the stretched coils of the helical coil 13 depending upon his immediate needs in navigating the vasculature or pushing across a stenosis.

In a typical method of using the invention, the physician forms a balloon dilatation catheter assembly by loading, preferably front loading the straightened distal end of the guidewire 10 into the proximal end of the catheter, the guidewire 10 through the balloon catheter and through the inner lumen thereof such that the guidewire is situated within at least a part of the distal inner lumen of the balloon catheter and lies adjacent the balloon catheter along the remaining length thereof. The balloon catheter assembly is then advanced through the guiding catheter which has already been advanced through the patient's vasculature and seated in the lumen of the target coronary artery. Once the guidewire assembly reaches the distal end of the guiding catheter, the guidewire is advanced out of the distal end of the balloon catheter and into the target coronary artery and an attempt is made to cross the stenosis. If the guidewire is unable to push across lesion, the physician uses the torquing means 40 provided at the proximal end of the guidewire to apply tension to the core wire 11 which causes the helical coils 13 to stack and increases the stiffness of the distal tip of the guidewire. The now stiffer guidewire can then more easily be pushed across the occluded area. Once the tip of the guidewire is past the occlusion, the dilatation balloon can be advanced over the guidewire and positioned across the lesion to be dilated.

While the invention has been described herein primarily in terms of certain preferred embodiments directed to guidewires, various modifications can be made without departing from the scope thereof. For example, the variable stiffness distal end can also be employed in fixed wire dilatation catheters such as described in U.S. Pat. No. 4,582,181 (now Re 33,166).

What is claimed:

1. A torqueable guidewire having a shaped distal section with adjustable flexibility comprising:
   a) an elongated longitudinally movable core member having a shaped distal extremity, a proximal extremity, and a longitudinal axis extending through the core member wherein the core member is configured to transmit torque from the proximal extremity to the distal extremity;
   b) a center coil which has a distal end and a proximal end and which is disposed around the distal extremity of the movable core member and which is affixed to the movable core member at the distal end and proximal end;
   c) a helical coil having a length axially adjustable by compression and expansion, a flexibility relative to its length, a proximal portion, and a distal portion secured to the distal extremity of the longitudinally movable core member, wherein the helical coil is disposed about the center coil which is disposed around the core member and said helical coil is slidable with respect thereto;
   d) a shapeable distal section including the distal extremity of the movable core member, the center coil, and the helical coil, adjustable from a flexible shaped condition where said distal section is in an orientation that is not coaxial with a portion of the core member proximal to the distal section to a straightened stiffer condition where said distal section is in an orientation that is coaxial with a portion of the core member proximal to the distal section;
   d) an elongated tubular support member which has a proximal end and a distal end and which is disposed about the longitudinally movable core member and proximal to the helical coil, which is slidable with respect to the core member and which has the distal end configured to support the proximal portion of the coil; and
   e) a tensioner connected to the proximal end of the tubular support member configured to apply tension to the core member and substantially uniformly adjust the compression and axial length of the helical coil and stiffen the distal section of the guidewire and straighten the distal section to an orientation collinear with the core member longitudinal axis, by effecting relative longitudinal movement between the core member and the elongated tubular support member.

2. A torqueable guidewire having a shaped distal section with adjustable flexibility comprising:
   a) an elongated longitudinally movable core member having a shaped distal extremity, a proximal extremity, and a longitudinal axis extending through the core member wherein the core member is configured to transmit torque from the proximal extremity to the distal extremity;
   b) a helical coil having a length axially adjustable by compression and expansion, a flexibility relative to the length, a proximal portion, and a distal portion secured to the distal extremity of the longitudinally movable core member, wherein the helical coil is disposed about the distal extremity of the core member and is slidable with respect thereto;
   c) a shaped distal section including the distal extremity of the movable core member and the helical coil, adjustable from a flexible shaped condition where said distal section is in an orientation that is not coaxial with a portion of the core member proximal to the distal section to a straightened stiffer condition where said distal section is in an orientation that is coaxial with a portion of the core member proximal to the distal section;
   d) an elongated tubular support member which is disposed about the longitudinally movable core member and proximal to the helical coil, which is slidable with respect to the core member and which has a distal end configured to support the proximal portion of the coil; and
   e) tension means to apply tension to the core member and substantially uniformly adjust the compression and axial length of the helical coil by stacking the helical coil to thereby stiffen the shaped distal section of the guidewire and straighten the shaped distal section to an orientation coaxial with the core member longitudinal axis, be effecting relative longitudinal movement between the core member and the elongated tubular support member without causing deflection off the distal extremity away from the longitudinal axis of the core member.

3. The torqueable guidewire of claim 2 wherein at least a portion of the helical coil is expanded.

4. The guidewire of claim 2 wherein the helical coil forms an annular lumen about the longitudinally movable core member.

5. The guidewire of claim 4 wherein a center coil is slidably disposed around the distal end of the movable core member within the lumen of the helical coil and substantially along the length of the helical coil.

6. The guidewire of claim 2 wherein the elongated tubular support member includes a proximal section comprising a length of hypotubing having proximal and distal ends.

7. The guidewire of claim 6 wherein the tensioning means is secured to the proximal end of the hypotube to effect relative longitudinal movement between the core member and the elongated tubular support member.

8. The guidewire of claim 7 wherein the tensioning means to effect relative longitudinal movement has a distal portion and a proximal portion spaced a distance from each other with a rotating knob between the distal and proximal portions wherein rotating the knob changes the distance between the distal portion and the proximal portion of the tensioning means.

9. The guidewire of claim 6 wherein the elongated tubular support member has an intermediate coil secured to the distal end of the hypotube and an outer sleeve secured to an exterior portion of the intermediate coil.

10. The guidewire of claim 9, wherein the intermediate coil has a length of about 40 cm to about 44 cm.

* * * * *